United States Patent
Hayes et al.

(10) Patent No.: US 6,890,411 B1
(45) Date of Patent: May 10, 2005

(54) CONTROL OF FLOW AND MATERIALS FOR MICRO DEVICES

(75) Inventors: Mark A. Hayes, Chandler, AZ (US); Nolan A. Polson, Chandler, AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 09/701,662

(22) PCT Filed: Jun. 29, 1999

(86) PCT No.: PCT/US99/13340

§ 371 (c)(1),
(2), (4) Date: Nov. 30, 2000

(87) PCT Pub. No.: WO99/64851

PCT Pub. Date: Dec. 16, 1999

Related U.S. Application Data

(60) Provisional application No. 60/088,956, filed on Jun. 11, 1998.

(51) Int. Cl.[7] .............................................. G01N 27/453
(52) U.S. Cl. ...................... 204/601; 204/451; 204/453; 204/454; 204/604
(58) Field of Search ................................ 204/454, 450, 204/451, 453, 600, 601, 604

(56) References Cited

U.S. PATENT DOCUMENTS

| | | | | |
|---|---|---|---|---|
| 4,323,439 A | * | 4/1982 | O'Farrell | 204/468 |
| 5,116,471 A | | 5/1992 | Chien et al. | |
| 5,151,164 A | * | 9/1992 | Blanchard et al. | 204/451 |
| 5,200,050 A | | 4/1993 | Ivory et al. | |
| 5,340,452 A | | 8/1994 | Brenner et al. | |
| 5,453,382 A | | 9/1995 | Novotny et al. | |
| 5,482,608 A | * | 1/1996 | Keely et al. | 204/452 |
| 5,630,925 A | | 5/1997 | Pentoney, Jr. et al. | 204/604 |
| 6,428,666 B1 | * | 8/2002 | Singh et al. | 204/450 |

FOREIGN PATENT DOCUMENTS

| | | |
|---|---|---|
| WO | 9604547 | 2/1996 |
| WO | 9627793 | 9/1996 |

OTHER PUBLICATIONS

A Manz et al., "Electroosmotic Pumping and Electrophoretic Separations for Miniaturized Chemical Analysis Systems", J. Micromech. Microeng. 4, 257–265 (1994).

Manz et al., "Planar Chips Technology for Miniaturization and Integration of Separation Techniques Into Monitoring Systems", *Journal of Chromatography*, vol. 593 (1992) p. 253–258.

Harrison et al., "Capillary Electrophoresis and Sample Injection Systems Intergrated on a Planar Glass Chip", *Anal. Chem.*, vol. 64, p. 1926–1932 (1992).

Hori et al., "Electroconcentration by Using Countercurrent due to Pressurized Flow and Electrophoretic Mobility", *Anal. Chem.*, vol. 65, p. 2882–2886, (1993).

Yu et al., "Chemical Modification of Platinum and Gold Electrodes by Naphthoquinones Using amines Containing Sulphhydryl or Disulphide Groups", *J. Electroanal. Chem.*, vol. 291, p. 171–186, (1990).

* cited by examiner

*Primary Examiner*—Kaj K. Olsen
(74) *Attorney, Agent, or Firm*—Pitney Hardin LLP

(57) ABSTRACT

The present invention generally relates to methods and devices for the control of the movement of fluids and electrically charged sample components within those fluids. More particularly, the present invention permits exclusion or concentration of specifically chosen sample components within a fluid. The present invention provides an analytical device, either microchip- or capillary-based, having the means to exclude specific sample components of interest from a capillary or channel for the purpose of preconcentration or control of movement of sample components. Such a control system includes a means for controlling the flow of the fluid in the channel and the placement of an electrode at the immediate entrance of each channel on such devices so that material may be directly manipulated by effects of both bulk flow and electrically driven migration.

3 Claims, 9 Drawing Sheets

CONTROL OF FLOW AND MATERIALS FOR MICRO DEVICES

This application is a U.S. national stage entry of PCT/US99/13340 filed on Jun. 11, 1999, which claims the benefit of provisional application 60/088,956 filed Jun. 11, 1998.

INTRODUCTION

The present invention generally relates to methods and devices for the control of the movement of fluids and electrically charged sample components within those fluids. More particularly, the present invention permits exclusion or concentration of specifically chosen sample components within a fluid.

The present invention provides an analytical device, either microchip- or capillary-based, having the means to exclude specific sample components of interest from a capillary or channel for the purpose of preconcentration or control of movement of sample components. Such a control system includes a means for controlling the flow of the fluid in the channel and the placement of an electrode at the immediate entrance of each channel on such devices so that material may be directly manipulated by either or both of the effects of both bulk flow and electrically driven migration.

BACKGROUND OF THE INVENTION

Capillary zone electrophoresis (CZE) is an efficient analytical separation technique which utilizes differences in mobility of sample components in an electric field based on the electrical charge and molecular site and shape of the sample component. Conventional CZE systems typically comprise a buffer-filled capillary with outlet and inlet ends disposed in two reservoirs into which one sample is injected, a means for applying voltage to the capillary resulting in migration of the sample through the capillary, and a means for detecting the sample zone.

Sample injection systems and capillary zone electrophoresis channel systems have been integrated together on planar glass substrates for separation of sample components as described by Harrison et al. (1992, Anal. Chem. 64:19261932) and Seiler et al. (1993, Anal. Cem. 65:1481–1488). Additionally, capillary electrophoresis on microchips has been described by Manz et al., (1992, J. of Chromatography 593:253–258). Total chemical analysis systems (TAS) in which sample transport, chromatography or electrophoretic separations and detection are all performed have also been developed.

One of the limitations of conventional CZE is the extremely small amount of sample which must be used in order to obtain separation or resolution of sample components. The use of small volume samples results in low amount of sample components of interest representing a major limitation in the detectability of sample components. On the other hand, the larger the sample volume introduced into the capillary, the broader the sample component peaks will be. Attempts to increase injection sample volume typically leads to a breakdown in resolution due to broadening of the peaks attributable to individual sample components which one is actually trying to resolve or separate and possibly leads to generation of laminar flow inside the capillary.

A number of techniques have been developed for increasing the concentration of specific sample components of interest and narrowing the width of the injected sample. One such technique involves the use of a solid-phase adsorption medium followed by a sequential combination of pressure- and electrically-driven flows as described in U.S. Pat. No. 5,453,382. Using such a technique, the solution containing the sample component of interest is applied to the solid phase adsorption medium under conditions which permit sorption of the sample component of interest to the adsorption medium. The environment of the medium is then altered to promote desorption of the concentrated sample component and a voltage gradient is induced across the medium to induce electroosmosis. U.S. Pat. No. 5,340,452 also describes a similar method for increasing the concentration of sample components prior to electrophoresis by using an active material which selectively retains the sample components of interest at the inlet end of the capillary tube.

For some specialized samples, another obstacle to successful separation of components of a solution results from the low strength of the electric field in the buffer bordering the sample solution and the column buffer. To circumvent this problem, water or diluted buffer may be removed from the capillary or column using electro-osmotic flow while the sample components are stacked in a support buffer thereby concentrating the sample components in a sample with a minimum amount of laminar flow. Such a method is described in U.S. Pat. No. 5,116,471.

For a large volume samples in constrained containers, pressurized flow and countermigration can be used to increase the overall concentration as described by Hori et al. (1993, Anal. Chem. 65:2882–2286). The sample is introduced into a first vessel containing buffer which is connected to another vessel by a glass tube. An electrode extending into the first vessel applies a voltage to the sample while suction pressure is applied. The sample concentration increases throughout the first vessel rather than concentrating the sample in a discrete portion of that vessel because the applied potential field is unconstrained throughout the buffer volume. Because the concentration increase and electric fields are dispersed throughout the entire first vessel volume this technique is not applicable as a small volume injection/preconcentration technique. Moreover, this arrangement does not allow for micromanipulations such as electrophoretic separation within the vessel containing the concentrated sample.

Hence, none of the aforedescribed methods provide for concentration of sample components upon immediate introduction into a constrained small volume flow path which receives a fluid sample without the use of complicated systems such as discontinuous buffer systems and, in some instances, microengineered absorption devices. Accordingly, there exists a need in the art for more precise and efficient methods and devices for increasing the concentration of sample components of interest within a fluid sample while maintaining a consistent buffer and without microengineering absorption systems.

SUMMARY OF THE INVENTION

Accordingly, it is an object of the present invention to provide a novel, more efficient method for controlling the movement of fluids and electrically charged species, referred to as sample components, within those fluids which permits exclusion or concentration of specifically chosen species within a constrained fluid-flow path.

It is another object of the invention to provide an analytical electrophoretic arrangement including microchips or capillaries which excludes specific sample components of interest from a capillary or channel for the purposes of preconcentration or control of movement of materials.

It is a further object of the present invention to provide an arrangement in which preconcentration and manipulation is achieved within a single constrained flow pathway system. More particularly, the sample is preconcentrated in a portion of the constrained flow pathway and is manipulated as it travels through the pathway.

These and other objects of the invention are obtained by a method for controlling the movement of a specific sample component in a fluid sample comprising:

(a) providing a constrained fluid pathway having an inlet;
(b) introducing the fluid sample into the inlet of the constrained fluid pathway;
(c) providing an electrode mounted at the inlet of the fluid pathway, the electrode being entirely external to the constrained fluid pathway;
(d) applying voltage to the electrode to create a voltage gradient within the constrained fluid pathways to promote electrophoretic migration of the sample component; and
(e) adjusting the flow rate of the fluid approximately equal to and opposite to the electrophoretic migration of the sample.
(f) adjusting the electrophoretic migration rate to be approximately equal and opposite to the flow rate of the fluid.

wherein movement of the specific sample component ceases.

The invention further provides an electrophoretic apparatus for controlling the movement of an sample component in a fluid sample comprising:

(a) at least one constrained fluid pathway having an inlet and an electrode mounted at the inlet of the constrained fluid pathway and entirely external to the constrained fluid pathway; and
(b) a power supply for supplying a voltage to the electrode.

It is another object of the invention to provide an electrophoretic apparatus for controlling the movement of an sample component in a fluid sample comprising:

(a) at least one injection fluid pathway having an electrode mounted at the inlet of said the pathway;
(b) at least one separation fluid pathway having an electrode mounted at the inlet of said pathway;
(c) at least one power supply for providing voltage between the electrodes; and
(d) means for regulating the bulk flow within the channels.

The present invention can be utilized in methods and devices for manipulating, testing, probing, or analyzing sample fluids of any kind where fluid manipulations are utilized for preconcentration, chemical reaction, injection, detection, or movement, or cessation of movement, of components of interest in a sample fluid.

In one embodiment, the present invention is directed to an analytical device having a plurality of channels with electrodes placed at the immediate entrance of all or selected channels and a method for regulating the bulk flow within the channels. When the bulk flow is set approximately equal to and opposite the electrophoretic migration of specific sample components of interest, the movement of those specific sample components ceases. The introduction of an electric field between the electrodes within the channel, coupled with control of bulk flow, allows selected sample components of interest to be excluded or preconcentrated immediately upon introduction of the fluid sample into the channel.

BRIEF DESCRIPTION OF THE DRAWINGS

Further objects and advantages of the invention will be apparant from a reading of the following description in conjunction with the accompanying drawings, in which.

DETAILED DESCRIPTION OF THE PREFERRED EMBODIMENTS

The present invention provides novel methods and devices for exclusion or concentration of specifically chosen sample components within fluids through the control of fluid movement and electrophoretic migration of charged sample components within those fluids. Typically the fluid sample is delivered or injected into a restricted flow path such as a channel or capillary. For purposes of the present invention, the flow path is preferably less than 200 microns in diameter. Precise control of fluid manipulation, sample component movement and solution injection systems are accomplished by carefully controlling the voltage field gradients and the bulk flow within each channel on a micro-device.

The principle of electrophoretic focusing as a means of sample component exclusion from a capillary or channel can be applied to the microscale analytical device described herein. The apparatus and processes disclosed herein may be used on microchip instrumentation in conjunction with control fluid dynamics in channels formed into or onto semiconductor devices. As used herein, the term "microchip" includes a semiconductor device comprising silica or any other substrate which may be used in microfluidic devices, which may be used in or in conjunction with a computer.

The present invention also provides for the placement of an electrode at the immediate entrance of each channel on a micro-device so that material movement may be directly manipulated by electrically-driven migration, i.e., electrophoretic migration. The present invention also provides control of bulk flow of the fluid within the channel. Bulk flow may be positive or negative depending upon the magnitude and direction of electrically-driven flow, i.e., electroosmosis, or various other sources of flow such as pressure, convection, capillarity, etc. Voltage gradients may likewise be manipulated to provide electrophoretic migration in either direction.

The introduction of an electric field resulting in electrophoretic migration of a specific sample component, coupled with manipulation of bulk flow equal and opposite to electrophoretic migration, results in cessation of movement of those specific sample components. Thus, the independent control of these parameters provides for absolute control of movement of sample components within the fluid about a micro-device.

The method of the invention comprises as a first step, the introduction of a sample containing the sample component of interest into a channel or capillary that has been filled with buffer. Sample introduction may be accomplished using a syringe by which the sample solution is injected into the channel. Alternatively, the introduction of the sample can be performed according to standard procedures, including but not limited to the use of electroosmotic flow, electro-kinetic pumping, or pneumatic pumping.

Figure 1:
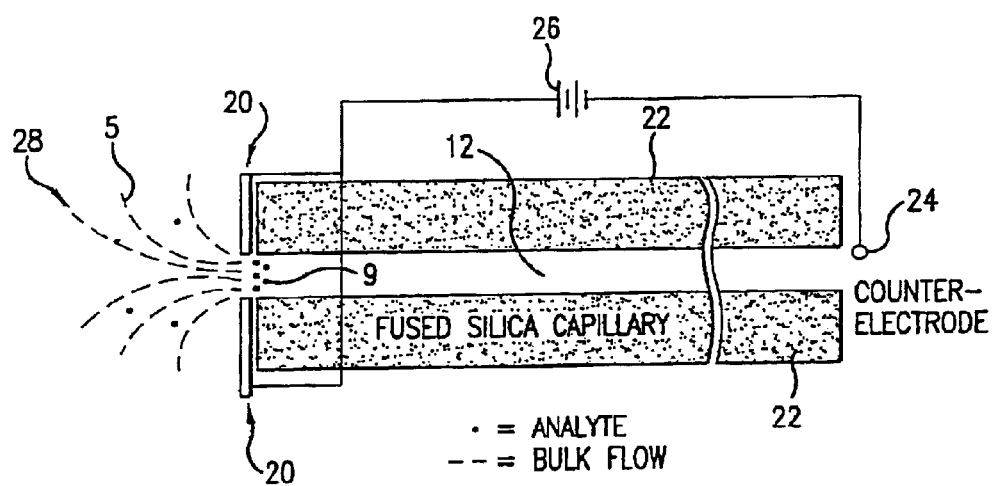
FIG. 1 is a schematic drawing of a fused silica capillary arrangement with electrodes placed immediately at the inlet to provide the voltage control within the capillary in accordance with the invention.

An electrophoretic arrangement in which a capillary is utilized to create the restricted flow path is shown in FIG. 1. In this arrangement electrodes 20 are located external to and mounted onto a fused silica capillary. A counter electrode 24 is placed at a location remote from electrodes 20 and forms a circuit therewith. A high voltage is applied to the electrodes 20 and 24 by power supply 26. A reservoir 28 including buffer bulk flow materials is in fluid contact with the capillary. A sample 5 including charged components is introduced into the reservoir and moves towards the entrance 9 of the capillary in the presence of the applied voltage which induces electrophoretic migration. Thus, the charged components in analyte 5 are concentrated at the entrance 9 of the capillary 22.

Figure 2A:
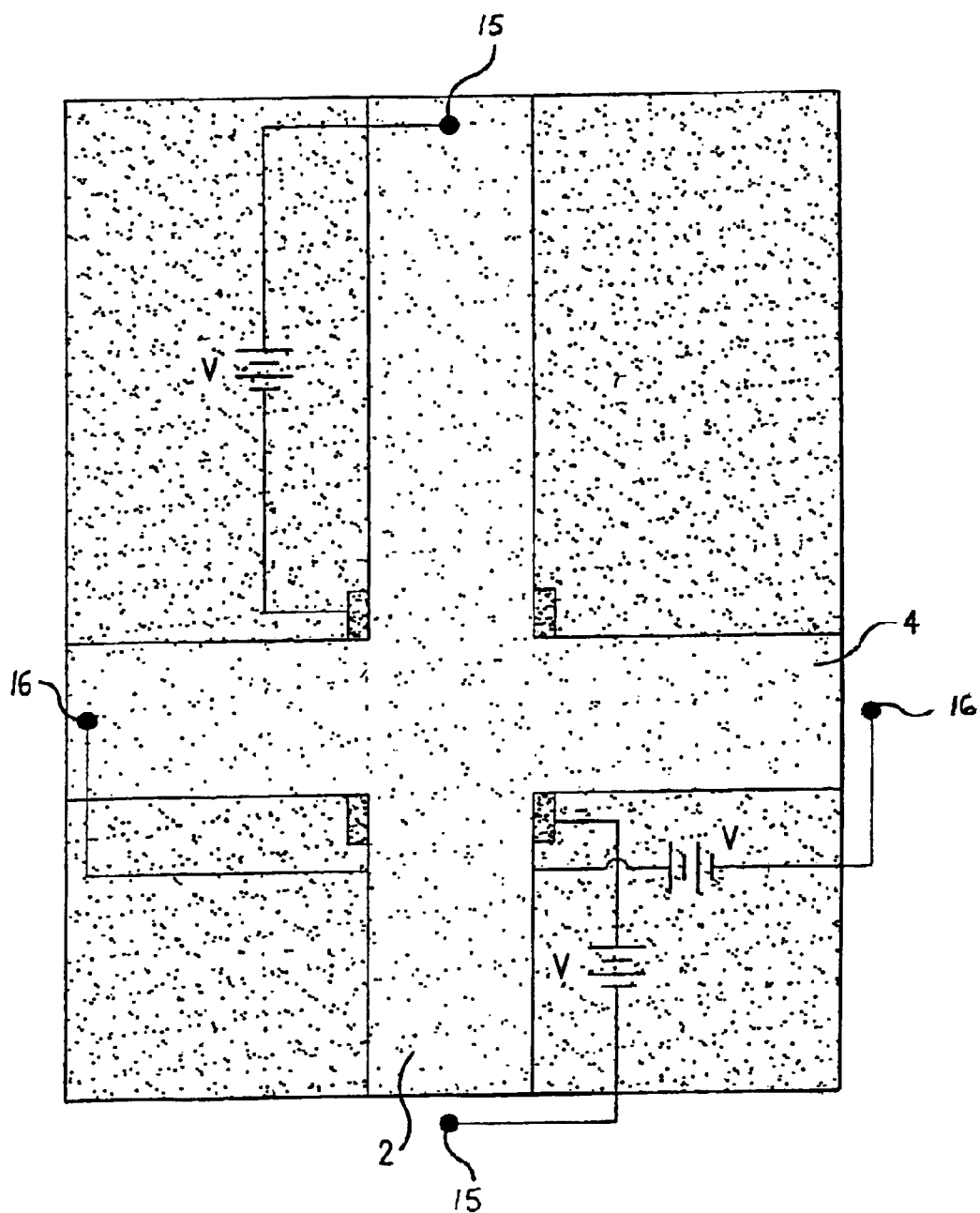
FIGS. 2(a), 2(b) and 2(c) are schematic drawings of a micro-device apparatus having an injection channel and a separation channel in accordance with the invention.
Figure 2B:
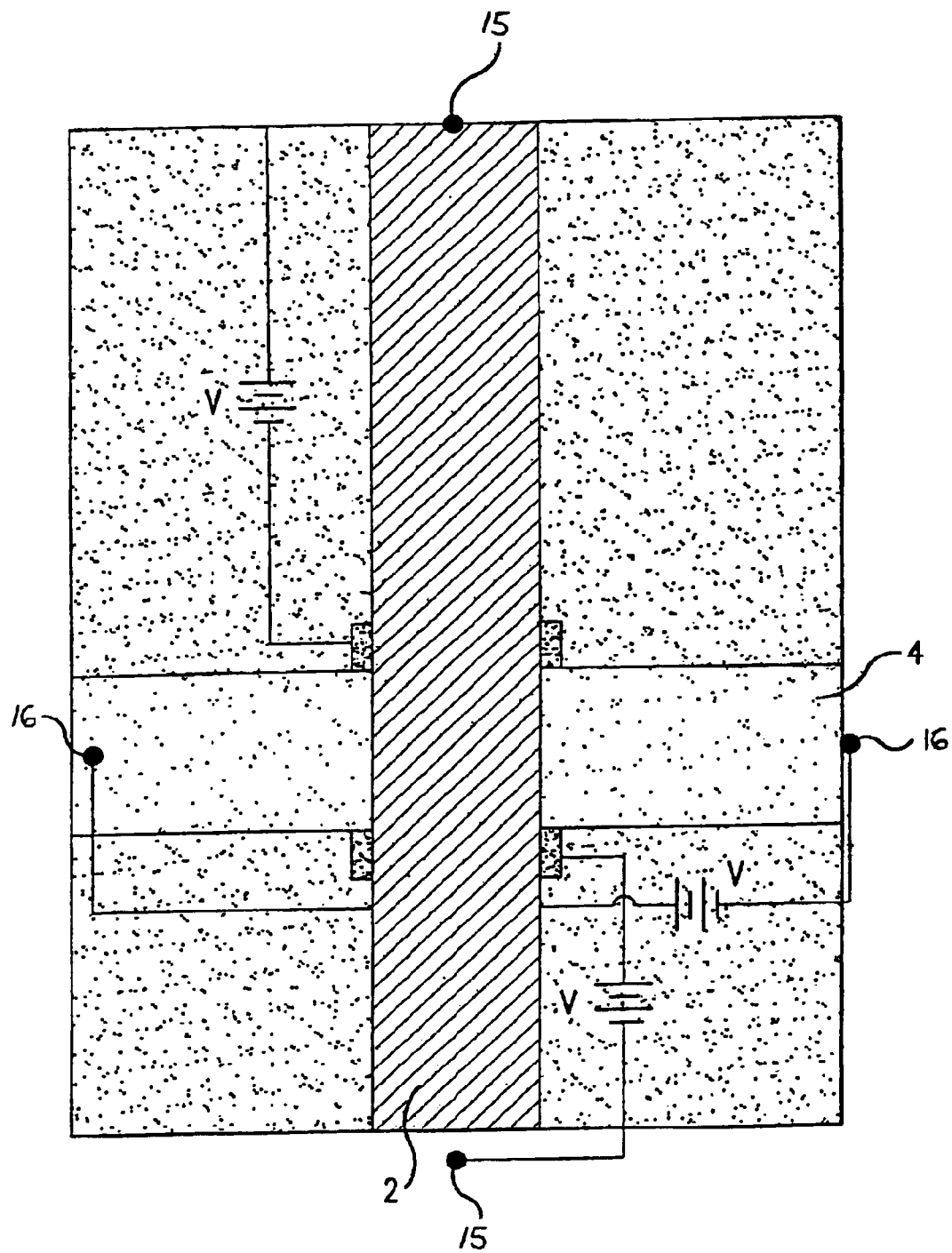
Figure 2C:
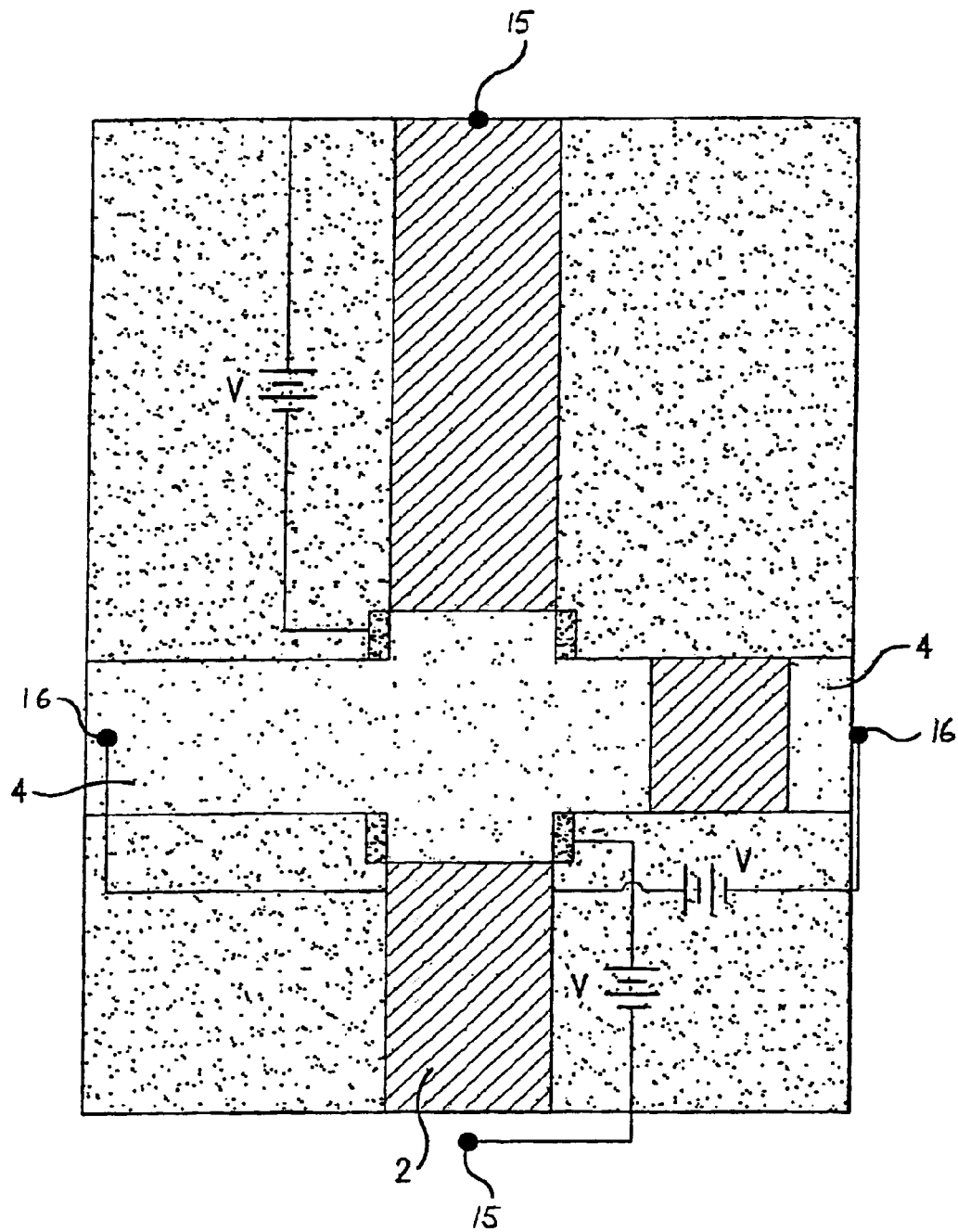

The present invention also provides a micro-analytical separation device comprised of etched or molded channels whereby various channels are used for separation and analysis purposes and others are distinctly used for the purpose of injection or material movement illustrated in FIGS. 2(a–c). As shown in FIG. 2a the system includes an injection channel 2 and separation channel 4. Sample material is injected to fill the injection channel 2 in between the separation channels 4 as depicted in FIG. 2b. To prevent unintentional introduction of material movement, commonly referred to as trailing or leaking, into the main separation channel after injection ceases, a small voltage is applied to the two injection channel electrodes 15. As illustrated in FIG. 2c, after the initial injection the electrodes are used to create an appropriate voltage gradient to prevent unwanted introduction of materials into the separation channel thereby concentrating desired components in separation channel 4. By manipulating flow and the voltage fields independently, positive, negative and neutral molecules may be manipulated as a group or individually.

A high voltage is applied by power supply means between the inlet and outlet end of the channel or capillary through electrode means. The voltage used is not critical to the invention and may vary widely depending on the sample component(s) to be excluded or concentrated. Conditions for selecting appropriate voltage conditions will depend on the physical properties of the sample component(s) and can be determined by those of skill in the art.

To preconcentrate sample components of either positive or negative charge, the method of the invention further comprises setting the bulk flow in the channel or capillary approximately equal to and opposite to the electrophoretic migration rate of the material. The bulk flow in the capillary may be generated and controlled by either electroosmosis, pressure or various other mechanisms. Bulk flow may be created and controlled by electroosmotic pumping devices, pneumatic devices, or directly by electroosmosis with dynamic control and monitoring. Thus the sample component of interest is drawn toward the channel by bulk flow, but is excluded from the channel by the voltage field effects on a narrow range of materials with similar electrophoretic migration rates thereby excluding or concentrating the sample component of interest at the immediate entrance of the capillary or channel.

Alternatively, any constrained fluid pathway, for example a fused silica or teflon capillary, where separation or injection of materials of interest are performed may be included in the device. Each channel or continuous fluid pathway where control of material movement is desired is constructed with an electrode adjoining the entrance and exit of the channel or pathway. Electrodes are placed at the entrance of the side channels to control the voltage field allowing electrophoretic migration to occur, and electroosmosis if the source of flow in the particular channel. In this manner the invention provides for integration of preconcentration and analysis within the constrained fluid pathway.

In the preferred embodiment of the invention as shown in FIGS. 2a–c, the injection channel 2 is perpendicular to the separation channel 4, although the geometry of this intersection is not of direct importance to the concepts presented here. Electrodes 15, 16 are located at the immediate entrances of channels 2, 4 and are electrically connected to the junction where the two channels 2, 4 intersect. Placement of an electrode at the immediate entrance of a capillary or channel and at the junction with another channel or buffer reservoir, creates a chemical voltage gate, in that movement of materials may be independently controlled by simply varying the voltage field gradient and the flow rate within the particular channel. At this chemical voltage gate, materials of interest may be totally excluded from entering the adjoining channel or selectively permitted to enter the channel by using electrophoretic focusing techniques.

Figure 3:
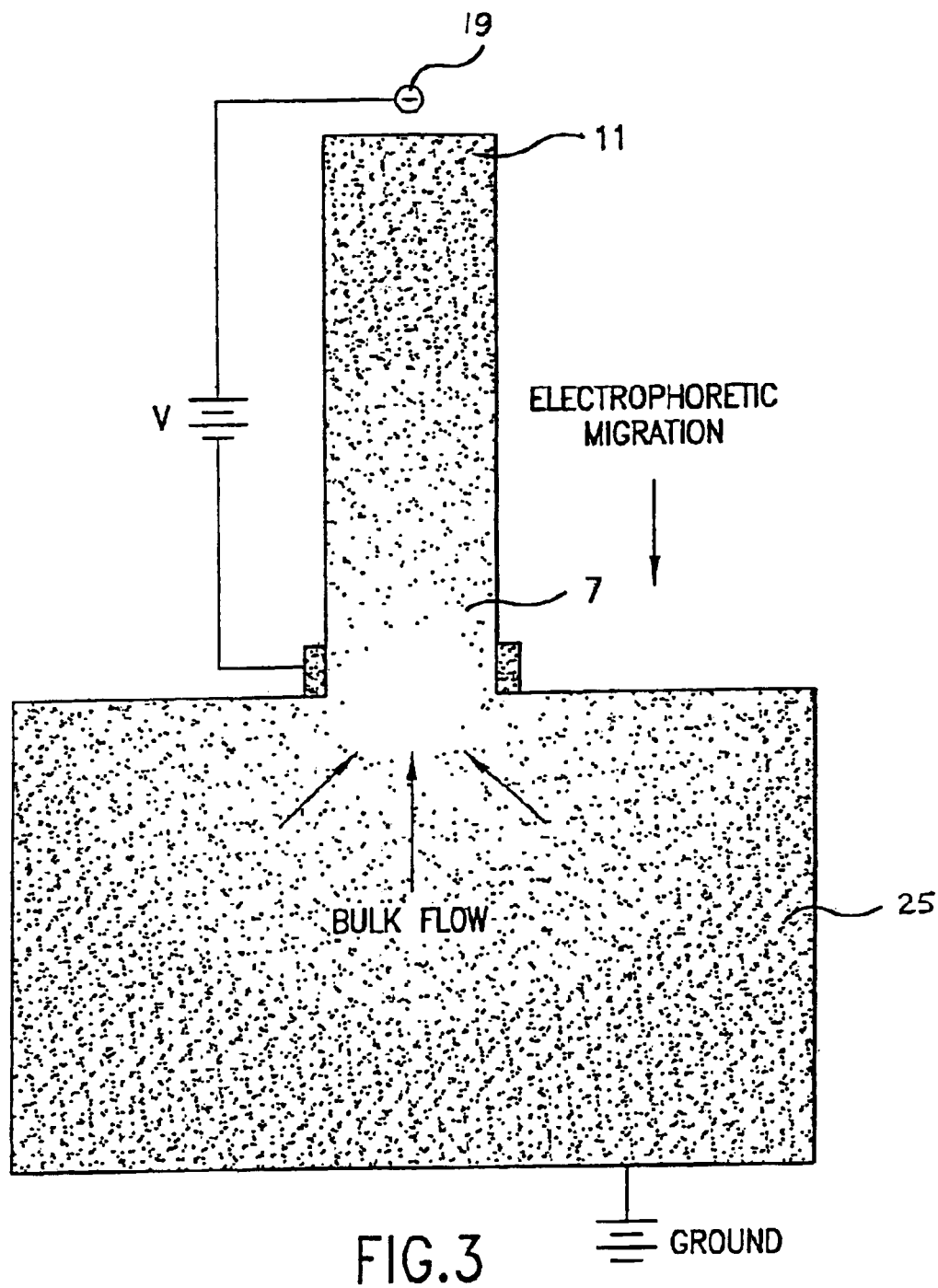
FIG. 3 is a schematic drawing of a micro-device apparatus indicating the preconcentration of materials at the immediate entrance to a channel where the voltage with in the buffer reservoir is held constant in accordance with the invention.

In another embodiment of the invention shown in FIG. 3 a reservoir containing a buffer solution 25 is placed in fluid contact with a channel 12 and an electrode 19 is placed at the immediate entrance to that channel 11. The buffer reservoir is maintained at the same voltage as the entrance electrode, thus the material will not undergo electrophoretic migration within the reservoir. However, the charged materials will move toward the channel entrance at the same rate as the bulk flow. At the immediate entrance of the channel the effects of the applied voltage field influences the charged materials, thus inducing electrophoretic migration. Since the bulk flow within the channel is approximately equal to and opposite the electrophoretic migration, the charged material of interest stops.

The flow rate of fluids may be controlled by, for example, the following techniques: pressure induced flow, capillary, and electroosmosis as taught by Giddings (1991, Unified Separations Science, Wiley-Interscience, New York. Chapt. 3). More specifically, pressure can be controlled by any physical or chemical means which will generate controllable flow or pressure. Capillarity can be controlled via chemical, electrochemical or photo-induced surface or solution changes as taught by Gallardo et al. (1999, Science 283:57–60). Electroosmosis can be controlled by external radial electrostatic fields as taught by Tsuda (1998, Handbook of Capillary Electrophoresis, Ed. J. P. Landers, $2^{nd}$ ed., CRC Press, Boca Raton, Chap. 22).

The methods and devices of the present invention may be used for purposes of manipulating, testing, probing, or analyzing fluids of any kind where fluid manipulations may be used for preconcentration, chemical reaction, injection, detection, or movement or restriction of movement, of the materials of interest. The manipulations provided for by the methods and devices described herein will allow for precise liquid injection and handling within a micro-chemical analysis device in addition to the ability to increase local concentration of materials by several orders of magnitude.

Preparation of specific embodiments in accordance with the present invention will now be described in further detail. These examples are intended to be illustrative and the invention is not limited to the specific materials and methods set forth in these embodiments.

The examples discussed hereinafter were conducted using the following standard chemicals and instrumentation, unless otherwise state:

Chemicals and Materials. Sodium dihydrogen phosphate and anhydrous ethyl alcohol (Aldrich Chemical Company, Milwaukee, Wis.); and phosphoric acid (EMG/NCV Science, Gibbstown, N.J.) were used as received. Capillaries were 45 cm in length (150 µm o.d.–20 µm i.d.) fused silica and were purchased from Polymicro Technologies (Phoenix, Ariz.). 0.2 µm carboxylate modified yellow-green fluorescent (505/515) latex micro spheres were purchased from Molecular Probes (Eugene, Oreg.). The capillary electrophoresis buffer used for the latex micro sphere experiments was 100 mM phosphate buffer, adjusted with phosphoric acid to pH 5.1.

Instrumentation. The capillary electrophoresis system was built and used a CZE1000R high voltage power supply from Spellman High Voltage Electronics Corporation (Hauppauge, N.Y.). The vacuum pump system was purchased from Cenco Hyvac (Fort Wayne, Ind.). The laser source was 442/325 nm 100 MPA: (Omnichrome Laser, Chino, Cat Scan). Image viewing was accomplished with a case closed-5E CCD camera (HutchNet, East Hartford, Construction) integrated to an Olympus Vanex stereo microscope (Tokyo, Japan). Data collection and analysis were accomplished using Labview software and an Imaq Pci-1408 image acquisition board by in-house program development (National Instruments, Austin, Tex.). Data analysis was also performed on Microsoft Excel spreadsheet program using an Optiplex GXI Pentium 233 (Dell Computer Corporation, Round Rock, Tex.). The fluorescent signal was monitored from the carboxylate modified latex micro spheres as vacuum and voltage fields were adjusted.

EXAMPLE 1

Figure 4:
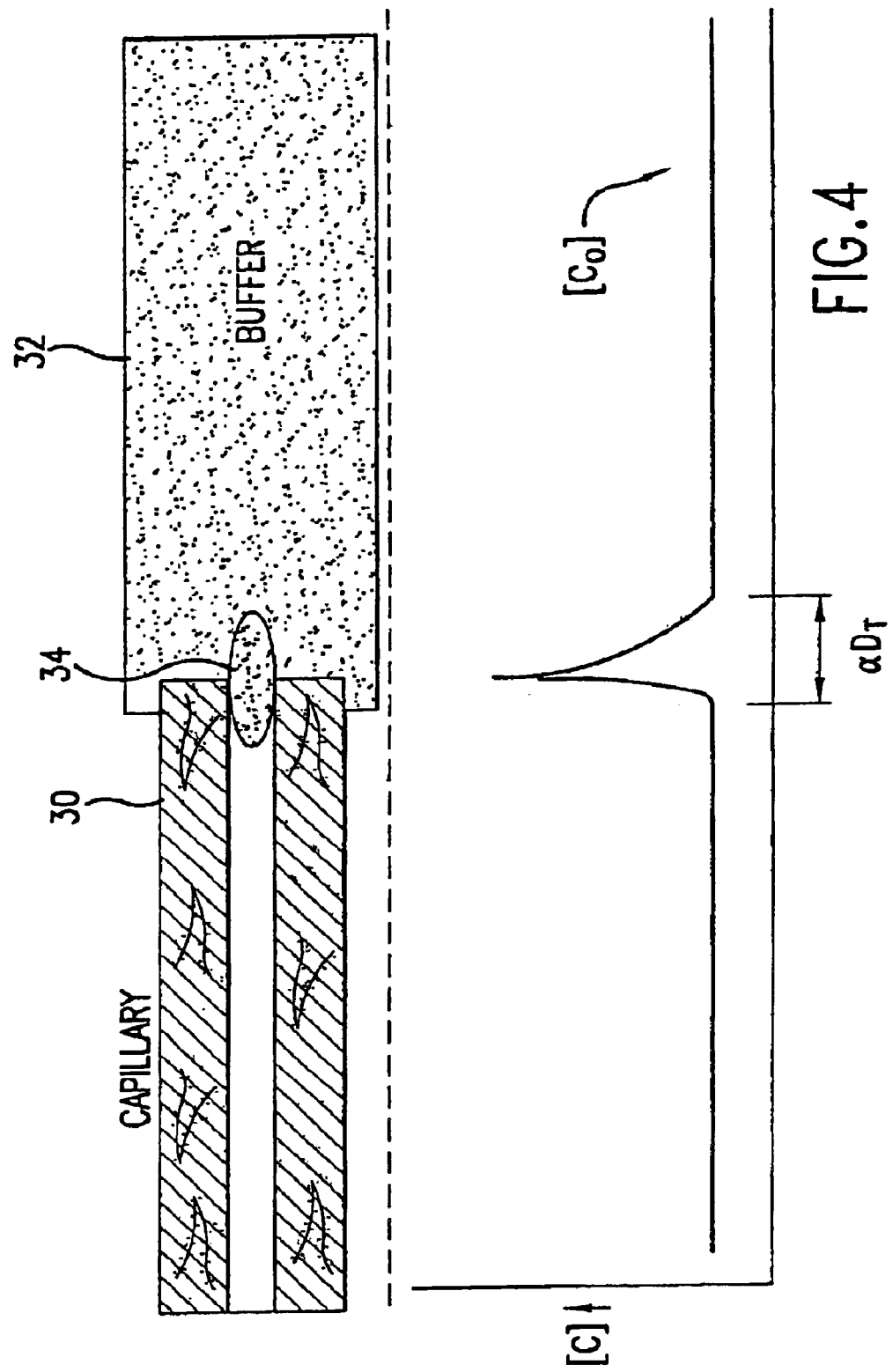
FIG. 4 is a schematic drawing of the theoretical profile of the preconcentration of material at the immediate entrance to a capillary showing the concentration of desired materials.

Experiments were performed to effectively demonstrate the increased local concentration of specific materials using a capillary 30 and reservoir 32 arrangement shown in FIG. 4. The tip of the capillary was coated with metal 34 thereby providing a metal electrode. These experiments were performed with fluorescence microscopy, fluorescently labeled latex microspheres, vacuum flow and a metal-coated capillary tip.

The presence or location of carboxylate-modified latex spheres were directly observed with the microscope under the effects of vacuum induced flow. The voltage was then empirically adjusted until the micro spheres were excluded from entering the capillary due to the electrophoretic migration rate of the micro spheres. The intensity of the fluorescent signal which is directly related to concentration was monitored. Only a selected probe area, of approximately 2.5 µm×120 µm parallel, and centered with the bore of the capillary immediately outside the entrance was quantitated for the fluorescence intensity changes.

Figure 5:
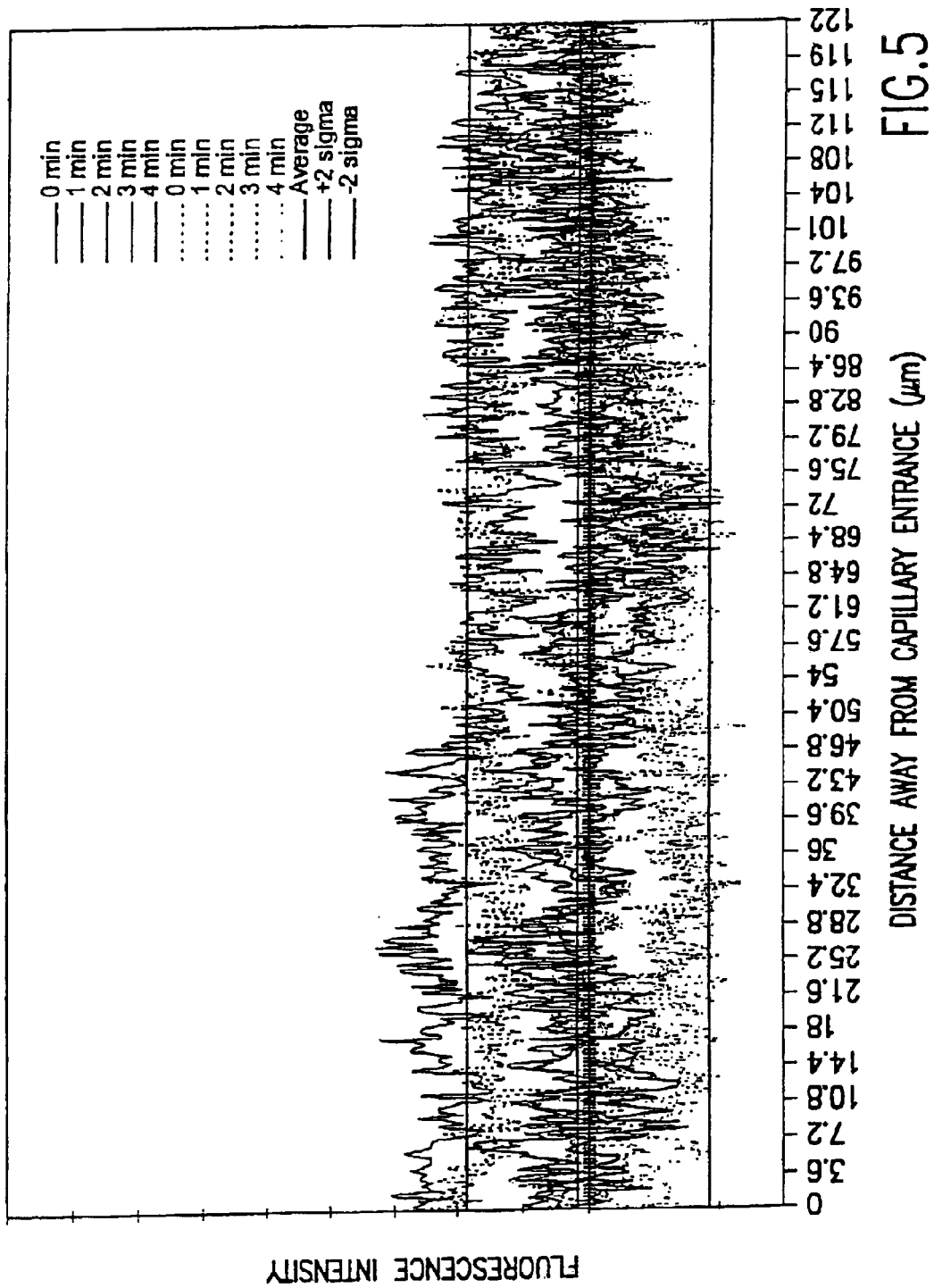
FIG. 5 is a graph showing the normalized fluorescence intensity versus distance outside the capillary entrance for two control experiments.
Figure 6:
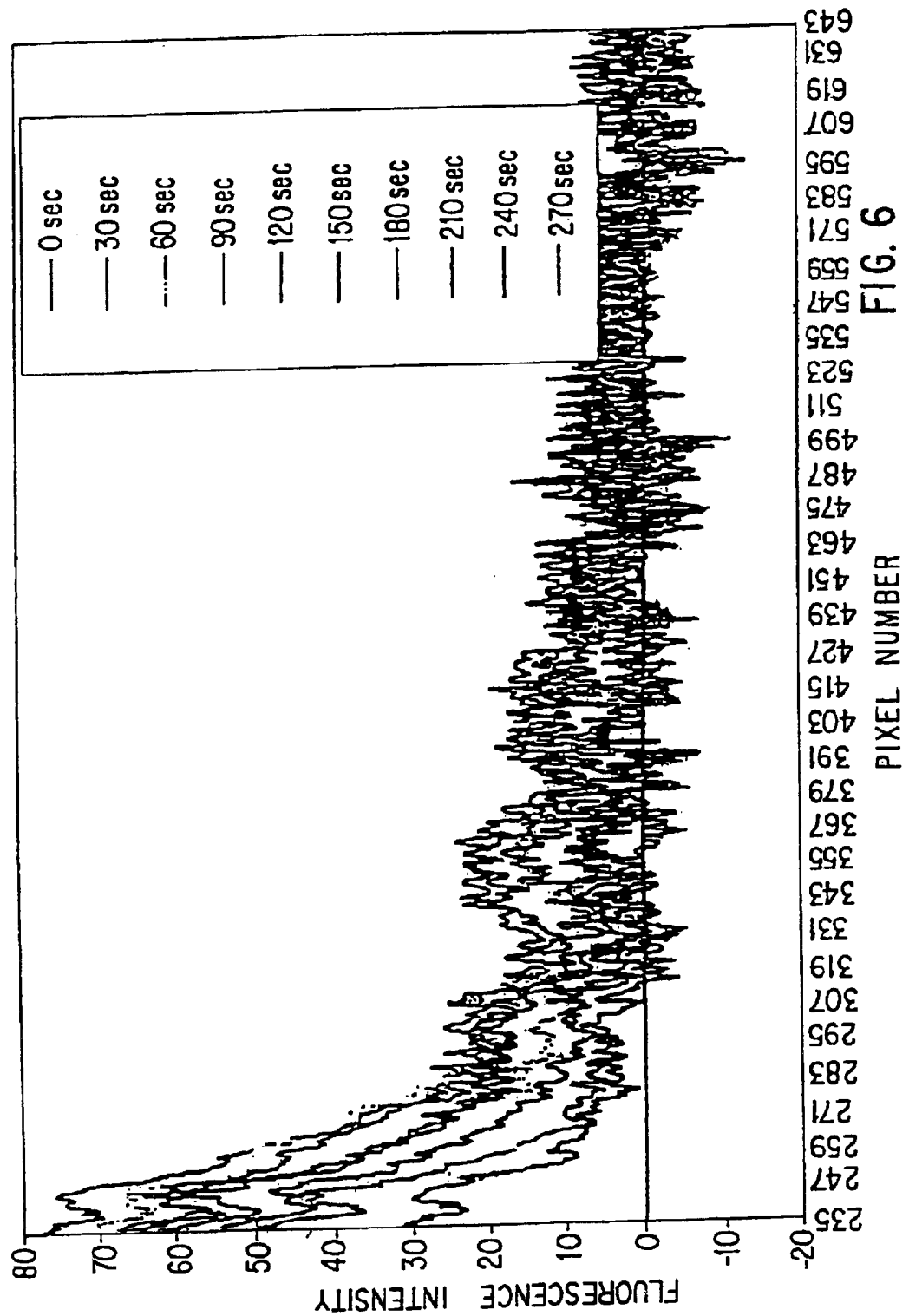
FIG. 6 is a graph showing the normalized fluorescence intensity versus number of pixels (1 pixel=0.24 $\mu$m) outside a capillary entrance.

First, control experiments were performed to determine if adsorption or other unknown processes were responsible for the increased fluorescence. These control experiments consisted of using either the voltage field only (−14 kV) or the vacuum-induced flow only 1.2 in Hg across as 45 cm long, 20 µm i.d. capillary. As illustrated in FIG. 5 the fluorescent signal was monitored and quantitated for 4 minutes. The fluorescent signal was normalized with the fluorescent signal obtained at t=0 minutes to eliminate any existing background fluorescence from the temporal data. The normalized fluorescent signal of the control experiments remained at a value of 1.75±9.32 (n=11) throughout the 4 minutes of the experiment (FIG. 6). No increase in fluorescent intensity was observed over the experimental period indicating that no unknown mechanisms nor adsorption to the capillary tip and walls contributed to the increased fluorescent intensity in the following experiments.

Figure 7A:
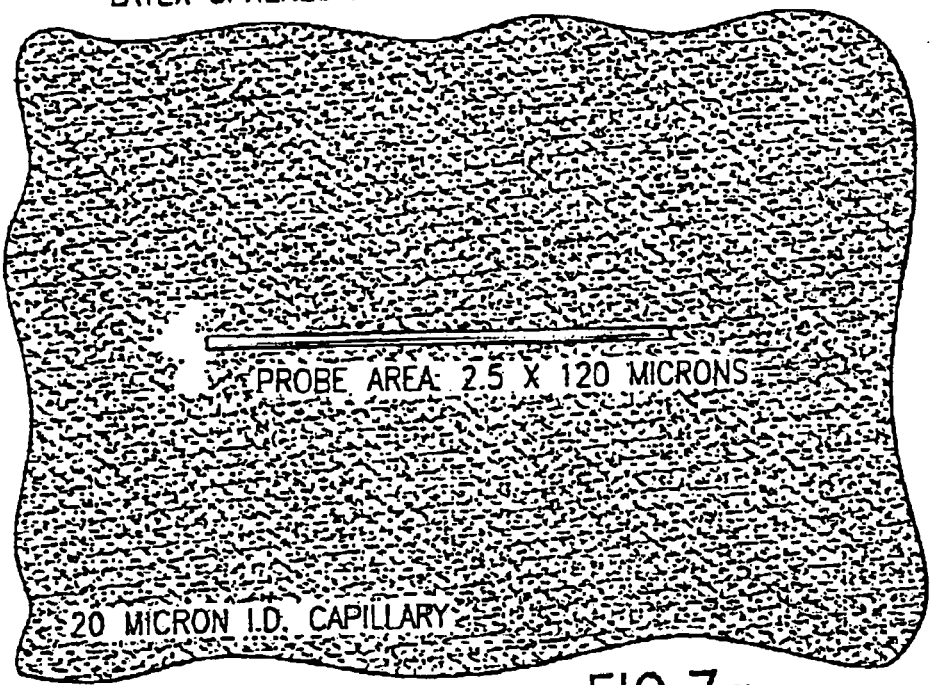
FIGS. 7(a) and (b) are fluorescence micrographs of a capillary entrance before and after, respectively, preconcentration of 200 nm fluorescently labeled latex micro spheres for 270 seconds.
Figure 7B:
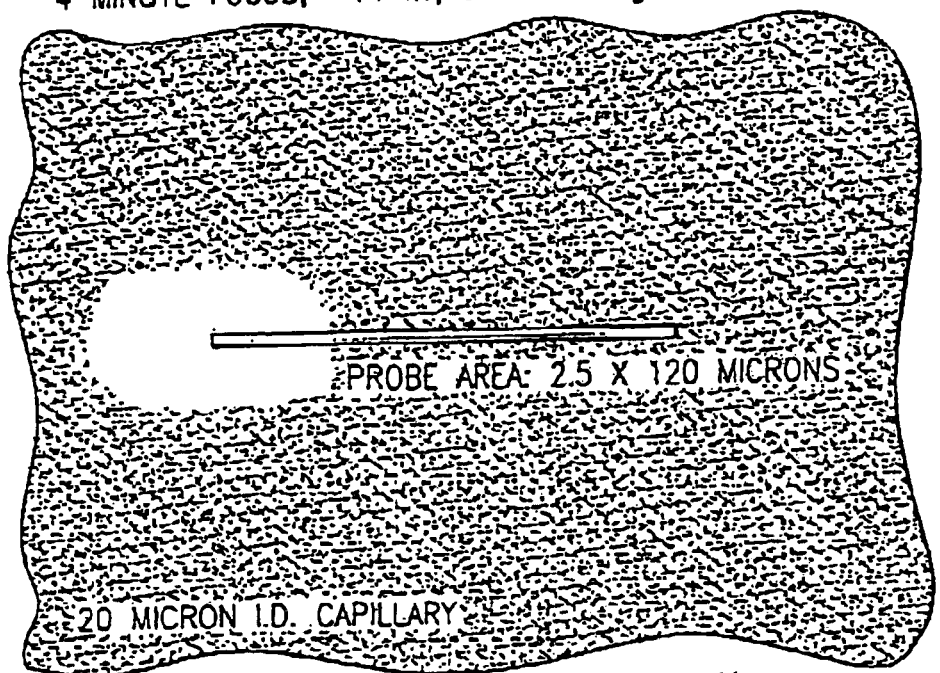

Experiments were performed to demonstrate preconcentration once the electrophoretic migration rate within the channel in the capillary was adjusted to be equal to and opposite the bulk buffer low rate. As with the control experiments, the fluorescence intensity was normalized and then monitored for 4 minutes (n=4). The voltage empirically determined to generate an electrophoretic migration rate which counterbalanced the bulk flow rate was 14 kV. FIGS. 7(a) and (b) are fluorescence micrographs of a capillary entrance before and after, respectively, preconcentration of 200 nm fluorescently labeled latex micro spheres for 270 seconds. As illustrated in FIG. 7b and FIG. 4 the largest fluorescence intensity changes occurred within 33 µm of the capillary entrance. Due to dynamic range limitations, the fluorescent intensity at the entrance to the capillary saturated the CCD and therefore quantitation of this effect must be performed some 19.2 µm outside the entrance to the capillary. The normalized fluorescent signal at 19.2 µm resulted in an increase in fluorescence intensity approximated by a linear equation (y=mx+b) where m is 0.042 arb. units/min and b is 0.99 arb. units ($R^2$=0.938, P≦0.01). The initial concentration of the micro-spheres was 1.473×10$^{10}$ micro spheres/mL.

The preconcentration build-up over time can be modeled as the formation as an exponential zone superimposed on a background of constant solute concentration for materials accumulating up behind a partially rejecting barrier such a filter. The filter in this case is the exclusion of the micro spheres from the capillary by the applied voltage field and the resulting electrophoretic migration rate. Assuming the system will reach steady state conditions after a given time, the background, concentration of the micro spheres is equal to $J_a/v$, initial flux over velocity. The concentration build-up of the micro spheres is given by the following equation:

$$c = J_a/v + (c_n - J_n/v)\exp(-|v|y/D_T)$$

where the concentration of the micro spheres is given by c, the flux of the micro spheres is given by $J_a$, the velocity of the flow towards the barrier is v, the original concentration of micro spheres is given by $c_n$, the distance from the barrier is given by y, and the total diffusion of the micro spheres is given by $D_T$. A plot of concentration of desired components versus location in the arrangement is shown in FIG. 4.

Although the present invention has been described with reference to latex micro spheres and fused silica capillaries providing the constrained fluid pathway, it should be understood that various modifications and variations can be easily made by those skilled in the art without departing from the spirit of the invention. Such modifications are intended to fall within the scope of the claims. Accordingly, the foregoing disclosure should be interpreted as illustrative only and not in a limiting sense. Various publications are cited herein, the contents of which are incorporated, by reference, in their entireties.

What is claimed is:

1. An electrophoretic apparatus for controlling the movement of a sample component in a fluid sample comprising:
   (a) at least one injection fluid pathway having an inlet;
   (b) a first electrode mounted at said inlet of said injection fluid pathway;
   (c) at least one separation fluid pathway having an inlet, said separation fluid pathway being in fluid communication with said injection fluid pathway at said inlet;
   (d) a second electrode mounted at said inlet of said separation fluid pathway;
   (e) at least one power supply for providing voltage to said first and second electrodes;
   (f) means for delivering said fluid sample having said sample component into said injection fluid pathway at a desired flow rate; and
   (g) means for adjusting said voltage on said first and second electrodes to an amount whereby said sample component electrophoretically migrates toward said second electrode at a rate equal and opposite to said flow rate of said fluid sample, so that the movement of said sample component in said fluid sample ceases at said inlet of said separation fluid pathway, and so that said sample component may be withdrawn through said separation fluid pathway.

2. The apparatus of claim 1 wherein said injection and separation fluid pathways are channels in a microchip.

3. The apparatus of claim 1 wherein said injection and separation fluid pathways are capillaries.

* * * * *